United States Patent
Pauley et al.

(10) Patent No.: US 6,595,974 B1
(45) Date of Patent: Jul. 22, 2003

(54) RAPID EXPANSION TAMPON PLEDGET

(75) Inventors: Suzanne M. Pauley, Dover, DE (US); Jeffrey Brown, Ramsey, NJ (US); Irwin Butensky, Teaneck, NJ (US); Dane R. Jackson, Bloomingdale, NJ (US)

(73) Assignee: Playtex Products, Inc., Westport, CT (US)

( * ) Notice: Subject to any disclaimer, the term of this patent is extended or adjusted under 35 U.S.C. 154(b) by 20 days.

(21) Appl. No.: 09/677,353

(22) Filed: Oct. 2, 2000

Related U.S. Application Data

(63) Continuation-in-part of application No. 09/414,764, filed on Oct. 7, 1999.

(51) Int. Cl.[7] .......................... A61F 13/15; A61F 13/20
(52) U.S. Cl. ................... 604/385.18; 604/904
(58) Field of Search ................. 604/904, 385.18; 28/118–121

(56) References Cited

U.S. PATENT DOCUMENTS

| | | |
|---|---|---|
| 1,884,089 A | 10/1932 | Millner |
| 2,330,257 A | 9/1943 | Bailey |
| 2,391,343 A | 12/1945 | Popper |
| 2,499,414 A | 3/1950 | Rabell |
| 2,884,925 A | 5/1959 | Meynier, Jr. |
| 3,431,909 A | 3/1969 | Krusko |
| 3,674,025 A | 7/1972 | Bleuer |
| 3,706,311 A | 12/1972 | Kokx et al. |
| 3,731,687 A | 5/1973 | Glassman |
| 3,738,364 A | 6/1973 | Brien et al. |
| 3,749,094 A | 7/1973 | Duncan |
| 3,762,413 A | 10/1973 | Hanke |
| 3,812,856 A * | 5/1974 | Duncan et al. |
| 3,815,601 A | 6/1974 | Schaefer |
| 3,834,389 A | 9/1974 | Dulle |
| 3,981,305 A | 9/1976 | Ring |
| 3,986,511 A | 10/1976 | Olofsson et al. |
| 4,018,225 A | 4/1977 | Elmi |
| 4,200,101 A | 4/1980 | Glassman |
| 4,211,225 A | 7/1980 | Sibalis |
| 4,212,301 A | 7/1980 | Johnson |
| 4,216,772 A | 8/1980 | Tsuchiya |
| 4,266,546 A | 5/1981 | Roland et al. |
| 4,300,561 A | 11/1981 | Kaczmarzyk et al. |
| 4,335,721 A * | 6/1982 | Matthews |
| 4,341,214 A * | 7/1982 | Fries et al. |
| 4,377,615 A | 3/1983 | Suzuki et al. |
| 4,475,911 A | 10/1984 | Gellert |
| 4,543,098 A | 9/1985 | Wolfe et al. |
| 4,627,849 A | 12/1986 | Walton et al. |
| 4,675,217 A | 6/1987 | Forsman |
| 4,714,466 A | 12/1987 | Dohzono et al. |
| 4,787,895 A | 11/1988 | Stokes et al. ............... 604/358 |
| 5,153,971 A | 10/1992 | Van Iten |
| 5,231,122 A | 7/1993 | Palumbo et al. |
| 5,350,371 A | 9/1994 | Van Iten |
| 5,364,383 A | 11/1994 | Hayes et al. |
| 5,476,455 A | 12/1995 | Silber |

(List continued on next page.)

FOREIGN PATENT DOCUMENTS

EP   0 062 948   10/1982

Primary Examiner—Dennis Ruhl
(74) Attorney, Agent, or Firm—Ohlandt, Greeley, Ruggiero & Perle, LLP

(57) ABSTRACT

There is provided a tampon pledget that expands without the aid of moisture or menses. The tampon pledget has a plurality of high resiliency, non-absorbent materials and a plurality of absorbent materials. The tampon pledget has improved comfort as compared to conventional fully compressed tampon pledgets. The tampon pledget preferably has all of its non-absorbent and absorbent materials enclosed in a coverstock. The coverstock may be inverted or turned inside out, prior to filling the coverstock with a plurality of non-absorbent and absorbent materials.

30 Claims, 3 Drawing Sheets

U.S. PATENT DOCUMENTS

| | | |
|---|---|---|
| 5,542,914 A | 8/1996 | Van Iten |
| 5,566,435 A | 10/1996 | Brown, Jr. |
| 5,659,934 A | 8/1997 | Jessup et al. |
| 5,755,906 A | 5/1998 | Achter et al. |
| 5,795,346 A | 8/1998 | Achter et al. |
| 5,817,077 A * | 10/1998 | Foley et al. |
| 6,039,716 A | 3/2000 | Jessup et al. |

* cited by examiner

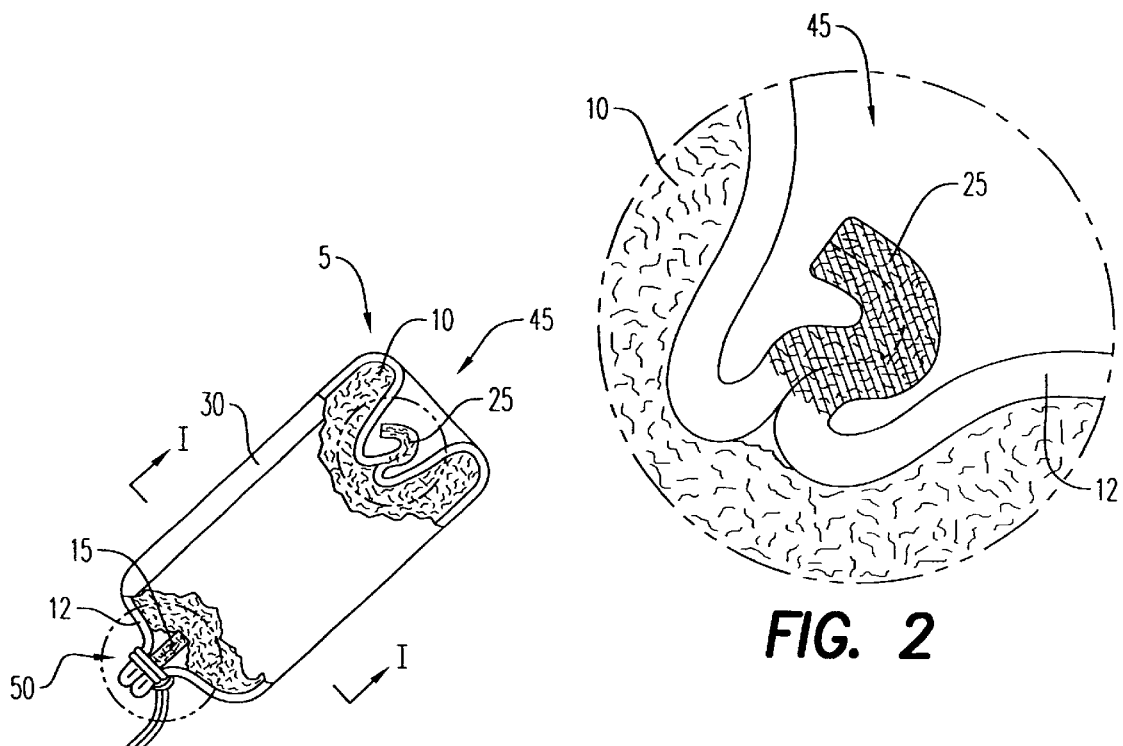
FIG. 2
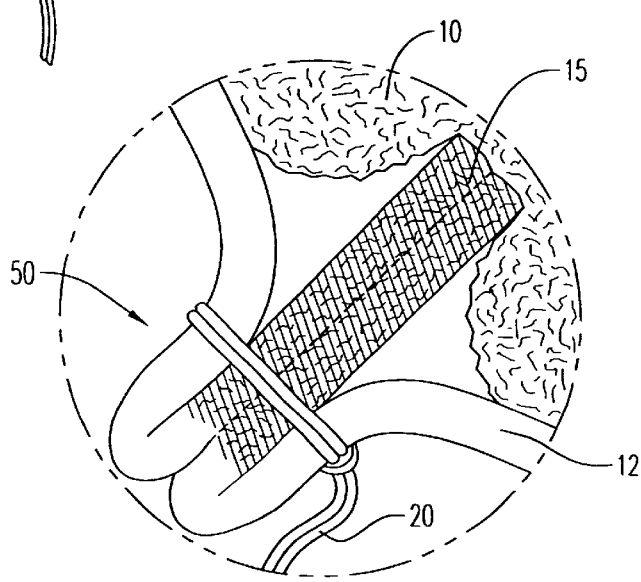
FIG. 1
FIG. 3
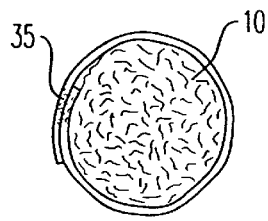
FIG. 5
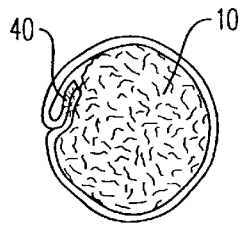
FIG. 6

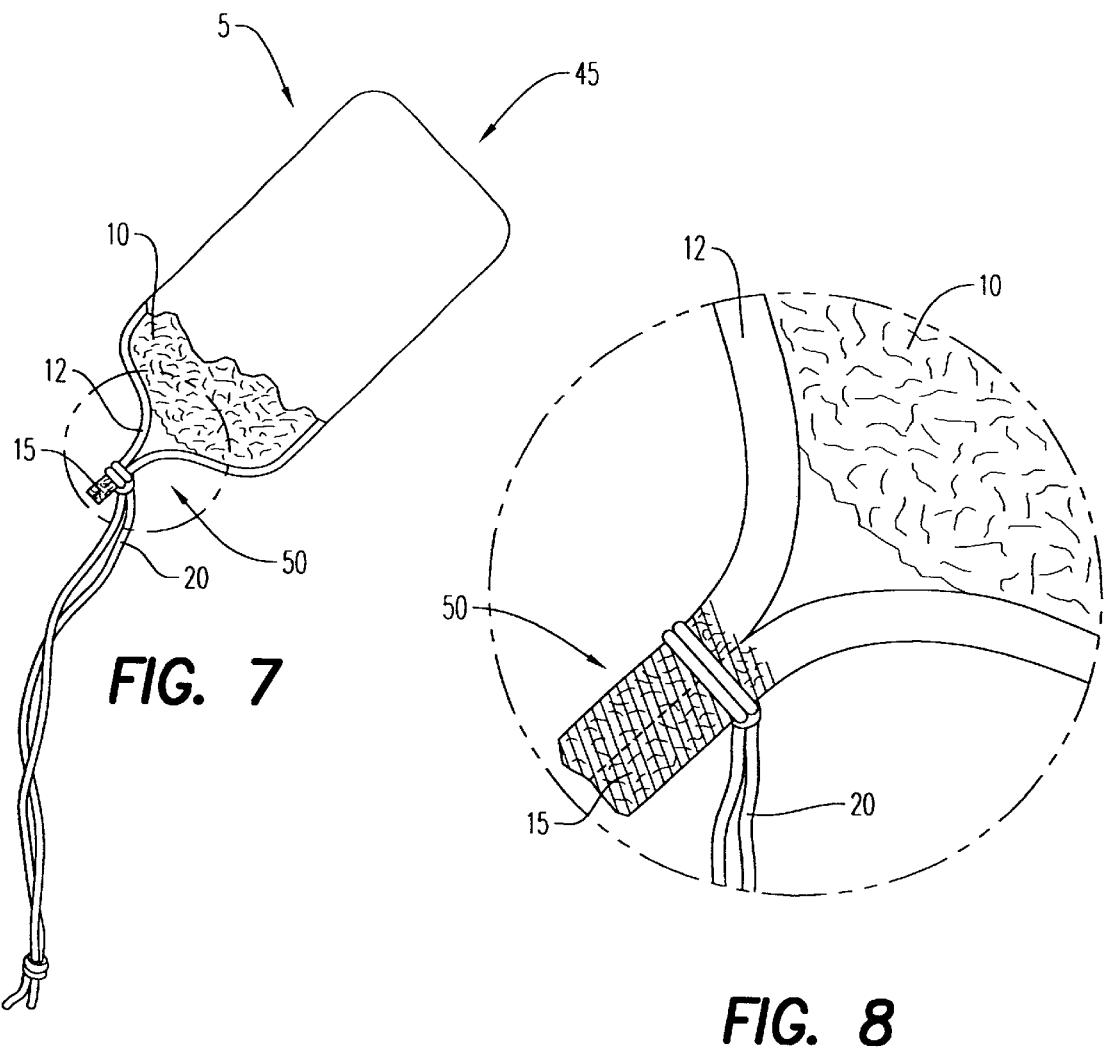

RAPID EXPANSION TAMPON PLEDGET

RELATED APPLICATION

This application is a continuation-in-part of U.S. application Ser. No. 09/414,764 filed on Oct. 7, 1999, pending.

BACKGROUND OF THE INVENTION

1. Field of the Invention

The present invention relates generally to an improved tampon or tampon pledget. More particularly, the present invention relates to a tampon pledget that expands rapidly when ejected from a tampon applicator, without the need for the tampon pledget contacting moisture or menses. Furthermore, the tampon pledget may have an inverted coverstock. Overall, the tampon pledget has improved comfort and good absorbency.

2. Description of the Prior Art

Tampon pledgets are typically compressed and set during either manufacture or placement of the pledget in a tampon applicator prior to use. In conventional tampon pledgets, the pledget's fibers will expand significantly upon initial contact with moisture, or menses once placed in a user's body. During expansion, the tampon pledget would conform to the user's body contours. Heretofore, it was thought that the tampon pledget needed to be ejected from the applicator and positioned within the user's body before expansion in order to achieve comfort.

Non-absorbent fibers have been used in a tampon pledget to provide expansion to the pledget. However, such tampon pledgets have not achieved the unexpected comfort of the tampon pledget of the present invention. Frankly, one would not think to improved comfort, and have comparable absorbency and sufficient bypass leakage protection, in a tampon pledget by combining non-absorbent and absorbent fibers. In addition, there has been a lack of appreciation that the correct ratio of non-absorbent fibers to absorbent fibers, including conventional absorbent fibers, provides improved comfort, and absorbency that is as good or better than known tampon pledgets.

In addition, the coverstock cylinder that encloses the absorbent material in a conventional tampon pledget typically does not totally enclose the absorbent material, leaving the absorbent material exposed at the ends of the tampon pledget. However, it is advantageous to totally enclose the absorbent material of the tampon pledget with the coverstock cylinder to ensure that the absorbent material remains intact. Therefore, the ends of the coverstock cylinder are gathered and bonded by means such as adhesive, heat, or ultrasonics, which result in hard seal bond areas. This hardness can be uncomfortable, especially during insertion and removal of the tampon pledget, where the hard seal bond areas may rub against the vulva-vaginal canal.

SUMMARY OF THE INVENTION

It is an object of the present invention to provide a tampon pledget that expands rapidly without the aid of moisture or menses.

It is another object of the present invention to provide such a tampon pledget that has improved comfort, and comparable or better absorbency, than known tampon pledgets.

It is still another object of the present invention to provide such a tampon pledget that has a plurality of non-absorbent materials and a plurality of absorbent materials.

It is a further object of the present invention to provide such a tampon pledget in which the plurality of non-absorbent and absorbent materials are distributed together in the pledget, or blended together in a certain percent ratio.

It is yet a further object of the present invention to provide such a tampon pledget that may have a coverstock.

It is still a further object of the present invention to provide such a coverstock that is inverted, or turned inside out.

These and other objects of the present invention will be appreciated from a tampon pledget that will expand without the aid of moisture or menses. The pledget comprises a plurality of non-absorbent materials, and a plurality of absorbent materials that are distributed or mixed with the plurality of non-absorbent materials. The tampon pledget preferably has all of its absorbent and non-absorbent materials enclosed in a coverstock. The coverstock may be inverted, or turned inside out, prior to filling the coverstock with a plurality of absorbent and non-absorbent materials.

The plurality of non-absorbent materials can be made from ribbon, cut film, high resiliency fibers, and combinations thereof. The plurality of absorbent materials can be made from powders, polymer beads, particulates, cellulosic fibers, superabsorbents, and combinations thereof.

BRIEF DESCRIPTION OF THE DRAWINGS

FIG. 1 is a partial plan view of a tampon pledget of the present invention;

FIG. 2 is a magnified view of the insertion end of the tampon pledget of FIG. 1;

FIG. 3 is a magnified view of the removal end of the tampon pledget of FIG. 1;

FIG. 5 is a cross-sectional view along line I—I in FIG. 1 of an alternate coverstock side seam;

FIG. 6 is a cross-sectional view along line I—I in FIG. 1 of a preferred coverstock side seam of the present invention;

FIG. 7 is a partial plan view of an alternate stringing of a tampon pledget; and FIG. 8 is a magnified view of the removal end of the tampon pledget of FIG. 7.

DETAILED DESCRIPTION OF THE INVENTION

Figure 4:
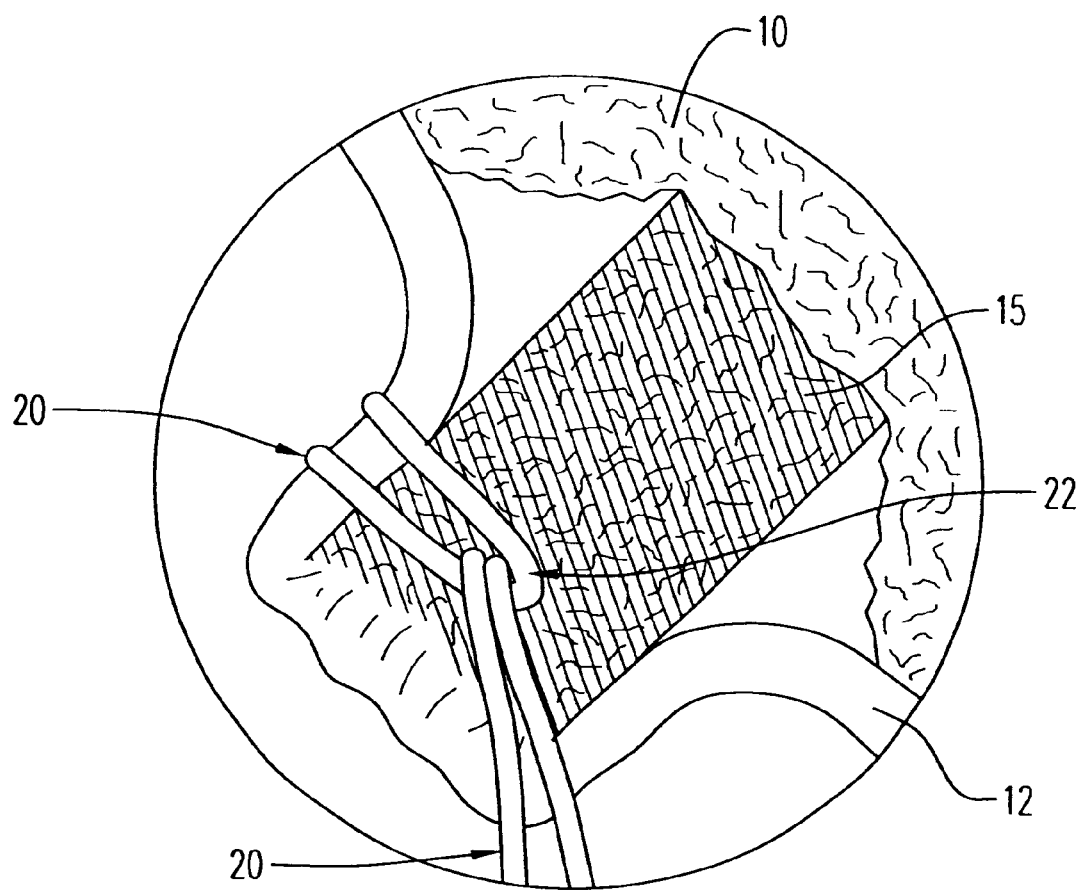
FIG. 4 is a magnified view of the removal end of the tampon pledget of FIG. 1, at a 90° rotation.

The tampon pledget of the present invention is called a dry expansion or fast blooming tampon pledget. The expansion of the tampon pledget is immediate upon release from a tampon applicator so that the expansion occurs entirely or primarily in its dry state. Thus, moisture or menses is not needed to expand the tampon pledget.

The expansion of the tampon pledget of the present invention in its dry state occurs faster than the expansion of a conventional or known, fully compressed tampon pledget when in contact with moisture or menses. Basically, the latter requires contact with moisture or menses to cause the fibers of the tampon pledget to expand, while the former does not, thus the dry expansion occurs immediately upon ejection from the tampon applicator due to the nature of the non-absorbent materials and the percent ratio of non-absorbent to absorbent materials in the tampon pledget. It is preferred that the non-absorbent materials be made from non-absorbent fibers having a wet modulus, measured at 5% extension, of about 10 gram/denier to about 60 gram/denier.

With such expansion immediately upon insertion into a user's body, it has unexpectedly been found that the tampon pledget of the present invention has improved comfort.

The length of the tampon pledget of the present invention is approximately the same length as a conventional or known tampon pledget, namely about two inches. Prior to expansion, the diameter of the present tampon pledget is also approximately the same as that of conventional tampon pledgets. However, the tampon pledget of the present invention, having the same length and initial diameter of such conventional tampon pledgets, expands on its own volition when ejected from the tampon applicator and before any moisture or menses is absorbed into the tampon pledget. The expansion of the tampon pledget is to a diameter larger than that of such comparable, conventional tampon pledgets. Thus, just prior to contact with moisture or the menses of the vagina, this tampon pledget has expanded into place.

The tampon pledget of the present invention is a combination or blend of non-absorbent materials and absorbent materials. The blend may be an amorphous blend. Suitable non-absorbent materials may be made from materials, such as, for example, ribbon, cut film, high resiliency fibers, and combinations thereof. Suitable absorbent materials may be made from materials, such as, for example, powders, polymer beads, particulates, cellulosic fibers, superabsorbents, and combinations thereof.

In a preferred embodiment, the absorbent and non-absorbent materials are made from fibers that are distributed together. The distribution could be a blending or mixing. The blending could be either randomly or as desired.

The distribution could also be by layers. For example, the non-absorbent fibers can be one layer sandwiched between two layers of absorbent fibers. Alternatively, there can be two layers with one layer being non-absorbent fibers and the other layer being absorbent fibers.

In an alternative, less preferred embodiment, the non-absorbent fibers are the core of the tampon pledget. The non-absorbent fibers are basically surrounded by the absorbent fibers.

The non-absorbent fibers urge the absorbent fibers outward from the center of the tampon pledget. Thus, the non-absorbent fibers are selected to provide high wet resiliency or springiness to the absorbent structures of the tampon pledget. Thus, the non-absorbent fibers are preferably curly, crimped or springy fibers.

Such non-absorbent fibers are polyester, polypropylene, polyethylene, aramid, nylon, acrylic, bicomponent fibers, and mixtures thereof. The polyester fibers are sold by Fiber Innovation Technology, Inc. under the tradename 4DG fibers. The 4DG fibers have a unique crenulated cross-section which results in deep grooves or channels along the longitudinal axis of the fibers. Preferably, the non-absorbent fibers are polyester, including, for example, 4DG fibers.

The non-absorbent fibers may, preferably, have a hydrophilic finish. It is preferred that the non-absorbent fibers are about 0.75 to about 30 denier fibers. More preferably, the non-absorbent fibers are a mixture of deniers. In a preferred tampon pledget, the mixture of non-absorbent fibers is 6 and 19 denier. When the non-absorbent fibers are a single denier, the fibers are preferable 15 denier.

The absorbent fibers can be any cellulosic fiber, such as, for example, rayon, lyocell, wood pulp, or cotton, or any superabsorbent, such as, for example, polyacrylate. The preferred absorbent fibers are rayon, superabsorbent or a combination of both fibers. The absorbent fibers are about 0.5 to about 30 denier. Preferably, the rayon fibers are about 1.1 to 1.5 denier and the superabsorbent fibers are about 9 denier. Alternatively, the superabsorbent may be in powder form or granular form, rather than a fiber.

In a more preferred tampon pledget of the present invention, the tampon pledget is made of 4DG non-absorbent fibers and rayon fibers.

The ratio of non-absorbent fibers to absorbent fibers is significant. It has been found that for optimum expansion and absorbency, the percent ratio of non-absorbent fibers to absorbent fibers is about 25/75 to about 70/30. In the more preferred tampon pledget of the present invention, namely 4DG and rayon, the percent ratio of non-absorbent fibers to absorbent fibers is about 40/60.

In an alternate embodiment of the present invention, the tampon pledget is made of 4DG non-absorbent fibers, and a combination of rayon and superabsorbent absorbent fibers. The inclusion of superabsorbent fiber appears significant to improve performance over the selection of just one type of absorbent fiber.

In the alternate embodiment, the percent ratio of rayon to superabsorbent fibers is about 70/30. Thus, in the alternate embodiment tampon pledget of the present invention, namely 4DG, rayon and superabsorbent (such as polyacrylate), the percent ratio of non-absorbent/rayon/superabsorbent fibers is about 40/42/18.

The fiber blend of the present invention may include a surfactant. The surfactant may be anionic, cationic, nonionic, or amphoteric. Preferably, the surfactant is non-ionic. The surfactant serves primarily as a process aid. It functions to dilute and disperse any fragrance that may be added to the tampon pledget. Also, the surfactant may effect uniform absorption of menses within the tampon pledget.

The nonionic surfactant may be, for example, one or more of the following: alcohol ethoxylates, alkylphenol ethoxylates, carboxylic acid esters, ethoxylated anhydrosorbital esters, glycerol esters, poly(oxyethylene-co-oxypropylene) based surfactants, polyoxyethylene fatty acid amines, polyoxyethylene fatty acid esters, and mixtures thereof. The preferred surfactant is a polyoxyethylene fatty acid ester. One such preferred surfactant is polysorbate-20, sold under the trade name Tween-20. The amount of surfactant added is between about 20 milligrams (mg) to about 140 mg per tampon pledget. Preferably, about 50 mg of surfactant is added per tampon pledget.

The tampon pledget of the present invention may also include additional additives, such as, for example, fragrance, odor absorbent, anti-bacterial agents, and combinations thereof.

The tampon pledget of the present invention has its insertion end recessed into the center of the pledget, and is crimped or compressed to a certain extent for insertion into a tampon applicator. The compression should be just enough so that the tampon pledget is "spring-loaded" in the tampon applicator. By way of example, if the inside diameter of the tampon applicator is about 0.600 inches, the tampon pledget should be compressed to a diameter of about 0.005 to about 0.020 inches less than the 0.600 inches, which is about 0.595 inches to 0.580 inches in diameter. Once ejected from the tampon applicator, the tampon pledget will expand rapidly preferably into an inverted bell-like shape configuration. The narrow end of this bell-shaped pledget has the removal string secured to it, while the other end of the tampon pledget forms the base of the bell.

Immediately after ejection from the tampon applicator (and before contact with any fluid or moisture), this tampon pledget has a free diameter at its widest point from about 25% to about 300% larger than just prior to ejection. Preferably, the tampon pledget has, immediately after ejection from the tampon applicator, a free diameter at its widest point about 225% larger than just prior to ejection.

The tampon pledget can also expand into a cylindrical shape, instead of a bell-shape if the insertion end is not initially tucked in.

The tampon pledget is preferably within a coverstock that encloses, preferably fully encloses, an amorphous blend of non-absorbent and absorbent fibers. The coverstock can be any conventional hydrophilic coverstock. However, the coverstock is preferably a non-woven, heat sealable coverstock, such as, for example, a surfactant-treated polyethylene/polypropylene bicomponent spunbonded coverstock.

Referring to FIGS. 1 and 3, it has been found that discomfort experienced during removal of the tampon pledget 5 can be minimized by inverting (turning inside out) the coverstock 12. In a preferred embodiment, the coverstock 12 is a flat sheet of coverstock that is rolled or formed into a cylinder with a seal along the longitudinal extant.

Referring to FIGS. 1, 5 and 6, the side seam 30 of the coverstock cylinder 12 is created by rolling flat coverstock into a tube. The side seam 30 is sealed by any conventional method known to those skilled in the art, such as, for example, adhesive, heat, or ultrasonics. As shown in FIG. 5, if the side seam 30 is an overlapped type seam 35, the inversion of the coverstock cylinder does not remove the hard seal from direct contact with the vulva-vaginal canal.

In a preferred embodiment of the present invention, shown in FIG. 6, an external fin seal 40 is formed prior to inverting the coverstock cylinder 12. The hard fin seal 40 is fully encased within the coverstock cylinder 12 upon inversion of the coverstock cylinder. Thus, the fin seal 40 is removed from direct contact with the vulva-vaginal canal resulting in greater comfort to the user during both insertion and removal of the tampon pledget 5.

Once the coverstock cylinder is formed, the coverstock at the removal end (i.e. the end receiving the removal string) is gathered and the removal end seal bond 15 is formed. Prior to filling the coverstock cylinder 12 with the blend of non-absorbent and absorbent fibers 10, and after the formation of the removal end seal bond 15, the coverstock cylinder 12 is inverted (turned inside out). The inversion of the coverstock cylinder 12 places the hard removal end seal bond 15 within the coverstock cylinder and removes the hard removal end seal bond away from direct contact with the vulva-vaginal canal. As a result, the user should experience greater comfort when removing tampon pledget 5.

Now referring to FIGS. 1 and 2, once the coverstock is inverted and filled with the blend of fiber, the coverstock is gathered at the insertion end 45 (i.e. the end distal of the removal end) and an insertion end seal bond 25 is formed. It is known that the gathered coverstock insertion end seal bond 25, at the insertion end 45 of the tampon pledget 5, may have the same degree of hardness as the removal end seal bond 15. This may result in discomfort during the insertion of the tampon pledget 5, as the insertion end seal bond 25 may rub against the vulva-vaginal canal.

In a preferred embodiment of the present invention, it has been found that by tucking the insertion end seal bond 25 below the surface of the tampon pledget's insertion end 45, in a perpendicular direction towards the removal end 50, the insertion end seal bond 25 no longer contacts the users body. Therefore, this may result in preventing or minimizing discomfort to the user during insertion.

The tampon pledget of the present invention includes a removal string secured to the removal end of the tampon pledget. The removal string may be made from any material known to those skilled in the art such as, for example, cotton, rayon, polyester, or combinations thereof. In addition, other suitable materials for the removal string include, for example, nylon, polypropylene, and combinations thereof.

If the material is in fiber form, it may be formed into a removal string by twisting, knitting, braiding, crocheting, or weaving. Alternately, the removal string may be formed by spinning a monofilament string directly from the material being used. The removal string may be treated with any antiwick agent, such as, for example, wax, to reduce the wicking potential of the removal string.

The cross section of the removal string does not have to be round. For example, a generally rectangular cross section, as in a woven ribbon, may also be acceptable.

To avoid breakage during the removal of the tampon pledget, the cumulative strength of the removal string(s), as attached to the tampon pledget, should be equal to or greater than the anchoring strength of the removal string to the tampon pledget.

In a preferred embodiment, the removal string is an antiwick treated, twisted (3 to 8 strands) cotton, with a linear weight of 0.2–0.8 grams per yard.

Referring to FIGS. 1 and 3, in a preferred embodiment, the removal string 20 is secured to the removal end seal bond 15. More specifically, referring to FIG. 4, the removal string 20 is looped and passed through the soft inverted coverstock 12 and then passed through the hard and strong flat area of the removal end seal bond 15. The removal string 20 is then passed back through the opposite side of the soft inverted coverstock 12. The loop is pulled back around and the free ends of the removal string are passed through the loop to form slipknot 22.

FIGS. 7 and 8 show an alternate stringing embodiment of the present invention where the coverstock 12 is not inverted.

By the inherent rapid, dry expansion of the tampon pledget of the present invention, the tampon pledget conforms during insertion more quickly to the user. Also, there is no need for moisture to contact the tampon pledget and be absorbed into the pledget to cause the expansion. The fact that the tampon pledget more quickly conforms to the user apparently results in the improved comfort.

The present tampon pledget having non-absorbent fibers, and especially the percent ratio of non-absorbent to absorbent fibers, and a hydrophilic, thermal bonded, bi-component, carded coverstock, has unexpectedly been found to achieve this improved comfort without loss of absorbency. For example, in a 102 women actual use test, 47% of the women preferred the tampon pledget of the present invention for "being comfortable to wear", as compared to just 26% for the Kotex® Security® super tampon.

The tampon pledget of the present invention has also been found to have absorbency about equal to or better than known tampon pledgets. A syngyna test was conducted pursuant to FDA specified test method, reference 21 CFR 801.430. The following is a table of the results of a syngyna test conducted in a laboratory. All tested tampons had a super absorbency classification.

| TAMPON TYPE | SYNGYNA ABSORBENCY (in grams) |
|---|---|
| Present pledget | 10.9 |
| Kotex ® Security ® | 11.2 |
| Playtex ® Silk Glide ® | 10.4 |
| Playtex ® Gentle Glide ® | 10.1 |
| Tampax ® | 9.7 |

Various modifications to the present invention may be made as will be apparent to those skilled in the art. Thus, it will be obvious to one of ordinary skill in the art that the foregoing description is merely illustrative of certain preferred embodiments of the present invention.

What is claimed is:

1. A dry expanding tampon pledget comprising:
   a plurality of non-absorbent fibers; and
   a plurality of rayon fibers and superabsorbent, wherein said plurality of non-absorbent fibers are blended with a plurality of rayon fibers and superabsorbent at a percent ratio of about 40% non-absorbent fibers, about 42% rayon fibers and about 18% superabsorbent.

2. The tampon pledget of claim 1, wherein said plurality of rayon fibers are about 0.50 to about 30 denier.

3. The tampon of claim 1, wherein said plurality of rayon fibers are about 1.1 to about 1.5 denier.

4. The tampon of claim 1, wherein said superabsorbent is in the form selected from the group consisting of powder, granular, fiber, and any mixtures thereof.

5. The tampon pledget of claim 1, further comprising a coverstock.

6. The tampon pledget of claim 5, wherein said coverstock is inverted.

7. The tampon pledget of claim 1, further comprising a surfactant.

8. The tampon pledget of claim 7, wherein said surfactant is nonionic surfactant.

9. The tampon pledget of claim 8, wherein said nonionic surfactant is selected from the group consisting of one or more alcohol ethoxylates, alkylphenol ethoxylates, carboxylic acid esters, ethoxylated anhydrosorbital esters, glycerol esters, poly(oxyethylene-co-oxypropylene) based surfactants, polyoxyethylene fatty acid amines, polyoxyethylene fatty acid esters, and mixtures thereof.

10. The tampon pledget of claim 9, wherein said surfactant is polyoxyethylene fatty acid ester.

11. The tampon pledget of claim 10, wherein said surfactant is polysorbate 20.

12. The tampon pledget of claim 7, wherein said surfactant is present in an amount about 20 mg to about 140 mg per tampon pledget.

13. The tampon pledget of claim 7, wherein said surfactant is present in an amount about 50 mg per tampon pledget.

14. The tampon pledget of claim 1, further comprising fragrance, odor absorbent, or a combination thereof.

15. A dry expanding tampon pledget comprising:
    a plurality of non-absorbent fibers;
    a plurality of absorbent fibers, wherein said plurality of non-absorbent fibers and said plurality of absorbent fibers are blended together and provide a percent ratio, wherein the percent ratio of said plurality of non-absorbent fibers to said plurality of absorbent fibers is about 25/75 to about 70/30; and
    an inverted coverstock having an interior surface adjacent with the blend of absorbent and non-absorbent fibers and an exterior surface opposite the interior surface, wherein said coverstock has an insertion end bond, a removal end bond, and a side seam bond, and wherein said removal end bond is on the interior surface of the inverted coverstock away from the user's body.

16. The tampon pledget of claim 15, wherein said percent ratio is about 40/60.

17. The tampon pledget of claim 15, wherein said side seam bond is formed from an external fin seal.

18. The tampon pledget of claim 17, wherein said side seam bond formed from said external fin seal is within said inverted coverstock away from said user's body.

19. The tampon pledget of claim 15, wherein the tampon pledget has an insertion end and a removal end opposite the insertion end, and wherein the insertion end bond is tucked inward below a surface of the insertion end in a direction perpendicular to the removal end of the tampon pledget.

20. A dry expanding tampon pledget comprising:
    a plurality of non-absorbent fibers;
    a plurality of absorbent fibers, wherein said plurality of non-absorbent fibers and said plurality of absorbent fibers are blended together to provide a percent ratio, wherein the percent ratio of said plurality of non-absorbent fibers to said plurality of absorbent fibers is about 25/75 to about 70/30;
    an inverted coverstock having an interior surface adjacent with the blend of absorbent and non-absorbent fibers and an exterior surface opposite the interior surface, wherein said coverstock has an insertion end bond, a removal end bond, and a side seam bond, and wherein said removal end bond is on the interior surface of the inverted coverstock away from the user's body; and
    a surfactant.

21. The tampon pledget of claim 20, wherein said surfactant is selected from the group of nonionic surfactants consisting of one or more alcohol ethoxylates, alkylphenol ethoxylates, carboxylic acid esters, ethoxylated anhydrosorbital esters, glycerol esters, poly(oxyethylene-co-oxypropylene) based surfactants, polyoxyethylene fatty acid amines, polyoxyethylene fatty acid esters, and mixtures thereof.

22. The tampon pledget of claim 21, wherein said surfactant is polyoxyethylene fatty acid ester.

23. The tampon pledget of claim 22, wherein said surfactant is polysorbate 20.

24. The tampon pledget of claim 20, wherein said surfactant is present in an amount about 20 mg to about 140 mg per tampon pledget.

25. The tampon pledget of claim 20, wherein said surfactant is present in an amount about 50 mg per tampon pledget.

26. The tampon pledget of claim 20, wherein said side seam bond is formed from an external fin seal.

27. The tampon pledget of claim 26, wherein said side seam bond formed from said external fin seal is within said inverted coverstock away from said user's body.

28. The tampon pledget of claim 20, further comprising fragrance, odor absorbent, anti-bacterial agent and combinations thereof.

29. A method of making a tampon pledget comprising the steps of:
    forming a tampon pledget;
    providing a virtually cylindrical coverstock;
    forming a removal end seal of said coverstock;
    inverting said coverstock after forming said removal end seal; and
    filling said coverstock with a plurality of non-absorbent and absorbent fiber.

30. The method of claim 29, further comprising the steps of:
    forming an insertion end seal;
    tucking said insertion end seal inward below a surface of a tampon pledget insertion end in a direction perpendicular to a removal end of the tampon pledget;
    securing a removal string to said removal end seal; and
    compressing the tampon pledget.

* * * * *